United States Patent [19]

Huffman

[11] 4,398,884
[45] Aug. 16, 1983

[54] DENTAL MODEL
[75] Inventor: Ronald E. Huffman, Tucson, Ariz.
[73] Assignee: KV33 Corporation, Tucson, Ariz.
[21] Appl. No.: 278,161
[22] Filed: Jun. 29, 1981

Related U.S. Application Data

[63] Continuation of Ser. No. 86,276, Oct. 19, 1979, abandoned.
[51] Int. Cl.³ .............................................. A61C 19/00
[52] U.S. Cl. ........................................ 433/74; 433/213
[58] Field of Search ........................... 433/74, 213, 60; 264/17

[56] References Cited

U.S. PATENT DOCUMENTS

| 2,619,725 | 12/1952 | Roeser | 433/60 |
|---|---|---|---|
| 2,700,219 | 1/1955 | Lindley | 433/60 |
| 3,470,614 | 10/1969 | Kelly | 433/36 |
| 3,518,761 | 7/1970 | Susman et al. | 433/74 |
| 3,798,772 | 3/1974 | Eberhard | 433/74 |
| 3,937,773 | 2/1976 | Huffman | 433/74 |
| 4,021,916 | 5/1977 | Spalten | 433/74 |
| 4,060,899 | 12/1977 | Sauter | 433/74 |

Primary Examiner—John J. Wilson
Attorney, Agent, or Firm—Cahill, Sutton & Thomas

[57] ABSTRACT

An insert is formed within a dental model to maintain alignment of seated and removably mounted model teeth of the dental model and to guide each removable model tooth during insertion into and withdrawal from the dental model. The insert includes a plurality of alignment studs captured by each model tooth on seating of same in the dental model and a pin extending from the model tooth into slidable engagement with a passageway in the insert to guide the model tooth during insertion and withdrawal. A method for developing the dental model is also disclosed.

3 Claims, 5 Drawing Figures

DENTAL MODEL

This is a continuation of application Ser. No. 86,276, filed Oct. 19, 1979, now abandoned.

The present application is related to U.S. Pat. No. 3,937,773, entitled "Method of Constructing Dental Models Using Guide Pins and Apertured Retainer", issued Feb. 10, 1976, assigned to the present assignee and describing an invention made by the present inventor.

The present invention relates to dental models and, more particularly, to guide means for removably seating model teeth in dental models.

In the field of dental care, false teeth are often retained in place by means of bridge work extending from the false tooth and anchored to adjacent healthy teeth. Other restoration techniques include the capping of badly decayed or deformed teeth with either parallel or full caps.

To accurately form and position the false teeth or caps, a dentist normally makes a negative impression of the affected tooth or teeth. The negative impression may be partial, unilateral or bilateral, depending upon the extent of the work to be done, and serves as a mold for developing a die of the patient's teeth and adjacent gum line.

Pursuant to the teaching of the prior art, the die may be formed in the following manner. A plurality of tapered dowels are positioned within the negative impression to correspond with the center of each cavity, which cavity represents an existing tooth. These dowels may be maintained in place by means of a plurality of positioning pins, as shown in U.S. Pat. No. 3,521,354. In the alternative, a jig assembly, such as shown in U.S. Pat. No. 2,851,728, may be used to properly position and orient the various dowels. To avoid the necessity for external and removable positioning pins or alignment devices, an alignment plate may be inserted within the negative impression, as described in U.S. Pat. No. 3,470,614. The alignment plate is permanently retained within the to-be-cast die and includes a dowel protruding therefrom to maintain alignment of the segregated cast teeth. Alternatively, a U-shaped retaining element, as described in U.S. Pat. No. 3,226,827, may be employed to maintain the dowels in place during casting of the die.

In an effort to overcome the need for external alignment mechanisms and devices, several alternatives have been developed. U.S. Pat. No. 3,286,350, teaches the insertion of individual dowels within each of the cavities of the impression. These pins must be manually aligned during setting of the die compound. Tapered dowels useful during such alignment are illustrated in U.S. Pat. No. 3,413,725. U.S. Pat. No. 3,478,428, teaches a base having a plurality of parallel tapered dowels extending upwardly therefrom. Here, the base is laid within the negative impression such that each of the pins extends into the die compound disposed within the negative impression.

After each of the above described dowels or dowel assemblies have been mounted within the negative impression with at least a portion of the dowel or dowels extending into the cavities representing the existing teeth, a die compound or pourable curable stone is poured into the negative impression until the latter is filled to a point approximating the patient's gum line. Thereby, at least a portion of each of the dowels is immersed within the poured compound and becomes a part thereof during the curing process. After curing, a wax or similar material is placed upon the cured stone surface. A further amount of die compound is then poured upon the cured stone to immerse the remaining parts of the dowels and form a base for the dental model. After the two resulting stone molds have been cured, the negative impression is removed. The composite mold structure is an exact duplication of the patient's teeth and adjacent part of his gums.

Removal of an individual tooth to prepare bridge work or a cap is accomplished by making vertical cuts on either side of the affected tooth down past the intersection of the two stone molds. The wax or similar material entrained intermediate the two stone molds permits facile separation therebetween; and, the reproduced tooth and adjacent gums may be severed from the base. The dowels extending downwardly from the tooth into the base are smooth surfaced and tapered to permit them to be easily broken loose from the base, to aid dislodgement of the dowels from the base, they may also be coated with wax or other release agent prior to the pouring of the die compound for the base. The tooth may be removed from the base and reinserted therein in a laterally correct position when the dowel is fully seated because of the guiding and aligning function served by the dowel.

In each of the above referenced patents, the alignment dowels are tapered. The taper of the corresponding depression in the base will allow dirt or other contaminants which may become deposited in the depressions to impede complete seating of the tooth. Without complete seating of the dowel(s), the tooth may not be correctly positioned. Because of the fracturable nature of the die compound used to make the dental model, repeated insertion and removal of the dowels will tend to fracture the depressions and result in a sloppy fit.

The prior art requirements for alignment of the pins is time consuming and is primarily dependent upon the skill of the particular dental technician, which level of skill variations may result in a high percentage of defective castings. Moreover, the prior art techniques do not automatically assure parallelism between the dowels. The lack of parallelism may result in difficulty when the selected tooth or teeth to be worked upon is to be removed. In U.S. Pat. No. 3,937,773, a pin retainer is cast into the base of the dental model for slidably receiving parallel non-tapered guide pins extending into the model teeth. Generally, two or more guide pins per tooth are employed in order to establish and maintain alignment of the model teeth with respect to the base of the dental model. The guide pin receiving passageways within the retainer are open ended to permit evacuation of any contaminates which may drop thereinto while the model teeth are removed from the dental model. Moreover, the passageways in the retainer are not subject to any appreciable wear and will continue to maintain any guide pins inserted therein in alignment.

While the dental model described in U.S. Pat. No. 3,937,773 is a substantial advance over the prior art, rough handling of the model teeth when removed from the dental model may result in loosening and misalignment of the multiple guide pins with respect to one another. Inaccurate alignment of the model tooth after seating may result as alignment is partly predicated upon the relative relationships between the guide pins.

It is therefore a primary object of the present invention to provide an insert for a dental model which incorporates a single pin for guiding a model tooth during withdrawal and insertion of the model tooth and a plurality of alignment studs for maintaining alignment of the model tooth on seating in the dental model.

Another object of the present invention is to provide an insert for a dental model which insert includes immobile model tooth alignment elements.

Yet another object of the present invention is to provide immobile alignment elements for precluding rotational movement of a removable model tooth seated in a dental model.

Still another object of the present invention is to provide a dental model with a plurality of fixed studs mating with commensurately sized and located depressions in a removable model tooth to retain the model tooth in alignment within the dental model.

A further object of the present invention is to provide a single pin for guiding a model tooth into and out of engagement with a dental model and immobile elements for aligning the model tooth on seating of the model tooth in the dental model.

A yet further object of the present invention is to provide a process for eliminating manual positioning of alignment and seating devices for removably retaining model teeth in a dental model during construction of the dental model.

A still further object of the present invention is to provide a process which eliminates the requirement for extensive technical skills in constructing dental models for accurately aligning removable model teeth therein.

These and other objects of the present invention will become apparent to those skilled in the art as the description thereof proceeds.

The present invention may be described with greater specificity and clarity with reference to the following drawings, in which.

Figure 1:
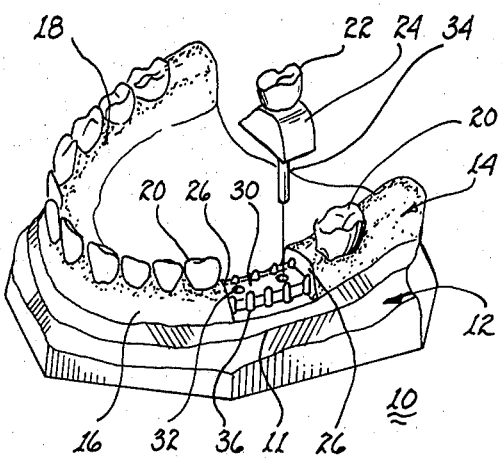
FIG. 1 illustrates a dental model having an insert formed therein.

In FIG. 1 there is shown a perspective view of a dental model 10 incorporating an insert for maintaining in alignment removable model teeth. The dental model includes a base 12 formed of readily commercially available pourable curable casting stone material. Die 14, which is duplicative of a patient's teeth and associated gum formation, is also formed of similar pourable curable casting stone material and separated from the base by a junction 11. The junction is developed by a film of wax or other release agent. Preferably, die 14 includes a reproduction of a part of the buccal and lingual walls, 16 and 18, as well as a reproduction of each of the patient's existing teeth 20.

For illustrative purposes, a single model tooth 22 and its associated gum formation 24 has been severed from die 14 by mesial and distal cuts, 26 and 28, respectively. These cuts have been made downwardly through die 14 to intersect and extend below junction 11 intermediate die 14 and base 12. Thereby, the model tooth may be readily separated from the base.

An insert 30 is disposed within die 10 and located so as to traverse junction 11 between base 12 and die 14. The insert includes a passageway 32 for receiving and guiding a pin 34 extending downwardly from gum formation 24 of the model tooth. A plurality of alignment studs 36 extend upwardly from insert 30 for mating engagement with commensurately configured depressions within the under surface of the gum formation; these depressions are developed during the molding of the dental model.

Figure 5:
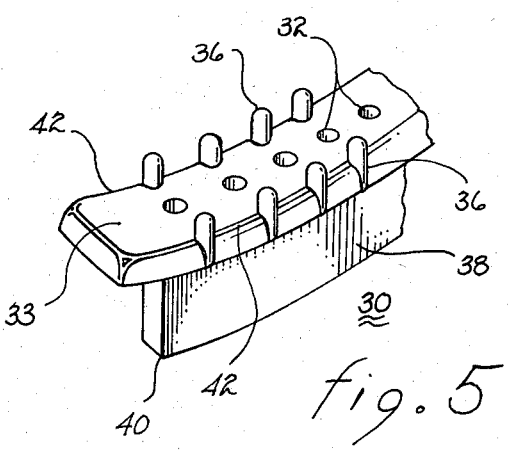
FIG. 5 is a perspective view of a section of the insert.

The construction, location and function of insert 30 will be described in further detail with joint reference to FIGS. 2, 3 and 5. Boradly stated, the function or purpose of insert 30 is that of providing a means by which a model tooth may be repetitively removed and replaced in an exact positional relationship within a dental model. Accordingly, the insert precludes misalignment or mispositioning in either the vertical or the horizontal plane of the model tooth with respect to the dental model. Additionally, the configuration of the elements defining the insert and the material thereof, such as nylon, are sufficiently wear resistant and stable to permit multiple cycles of removal and replacement of the model tooth. Should these conditions not be met with meticulous compliance, any caps or bridge work being performed upon the removable model tooth by a dental technician will be less than absolutely accurate and the patient will suffer commensurately.

Stability of insert 30 within dental model 10 is achieved by molding the insert into base 12 whereby it becomes an integral part of the base. Because the material used in dental models is fracturable by impact and as the insert is subject to some impacting by removal and replacement of the model tooth, transmission of the impact forces to the dental model and the eventually resulting fracturing thereof must be reduced. As the insert serves as a reference member to which two or more teeth are referenced with respect to vertical and horizontal alignment, the sections of the insert corresponding to each of the plurality of removable model teeth must remain in constant reference with respect to one another. Moreover, the guiding and alignment features attendant the insert must remain stable and uncontaminatable throughout the normal expected life of the dental model. The inserts illustrated in FIGS. 2, 3, 4 and 5 satisfies all of these criteria and parameters.

Figure 2:
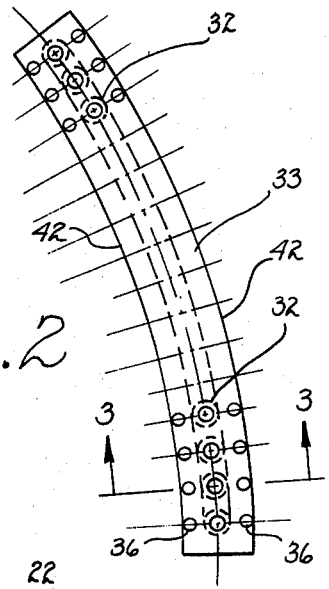
FIG. 2 is a top view of an insert positionable within a dental model.
Figure 4:
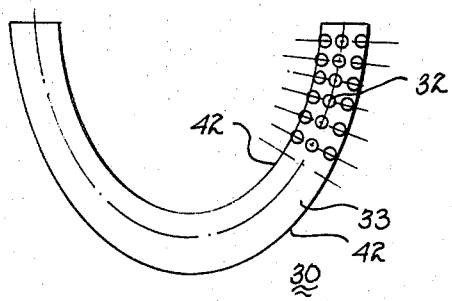
FIG. 4 illustrates a variant in configuration of the insert shown in FIG. 2.

Insert 30, as shown in FIG. 2, is a curved section which has been generalized in curvature to proximate the lateral curvature of the line of teeth extending from the molars to the cuspid. It is to be understood that differently curved inserts may be developed for differently shaped jaws or lines of teeth. In example, the insert illustrated in FIG. 4 is particularly adapted for use in conjunction with a bilateral dental model wherein the teeth of interest to the technician extend from approximately the front molars on one side to the front molars on the other side.

Insert 30 is formed with a T-shaped cross-section, which cross-section provides at least two distinct benefits. First, it minimizes the amount of material of base 12 removed to accommodate the insert and thereby helps maintain a generally substantial massiveness of the base for purposes of stability. Second, the multiple planes and resulting plane intersections adjacent the material of the base tends to more firmly lock or maintain the insert in fixed relationship to the base.

A plurality of passageways 32 extend from upper surface 33 of insert 30 through base 38 to bottom surface 40 of the base. A plurality of pairs of studs 36 are disposed along the lateral edges of the insert and in general alignment with one of passageways 32. The top lateral edge of the insert may be square or radiused as indicated by surface 42, as shown particularly in FIG. 3. Were surface 42 radiused to a radius approximately the thickness of the arm of the T-section, a better physical interlock between the insert and the adjacent removable model tooth is established. Studs 36 interlockingly mate with depressions 44 developed within removable model tooth 22 during the molding process of die 14. Pin 34, which may be of steel to slidably cooperate with the nylon material of the insert, is lodged within one of passageways 32 and extends from insert 30 to the interior of removable model tooth 22. The pin is lockingly engaged to the tooth (or gum formation 24) by a plurality of cuts 46 made in the upper end thereof, which cuts are filled with casting material during molding of die 14.

After the mesial and distal cuts are made, model tooth 22 is physically interconnected to the dental model through pin 34 lodged within passageway 32 and depressions 44 within which are disposed studs 36. Pin 34 is slidably but frictionally maintained within passageway 32 to prevent withdrawal of the pin and displacement of the removable tooth by incidental movement of the dental model. However, the primary purpose of pin 34 is that of guiding the removable model tooth into and out of engagement with studs 36. These studs, with some cooperation from pin 34, restrain the removable model tooth from lateral or rotational movement in the horizontal plane and rotational movement in the vertical plane.

Figure 3:
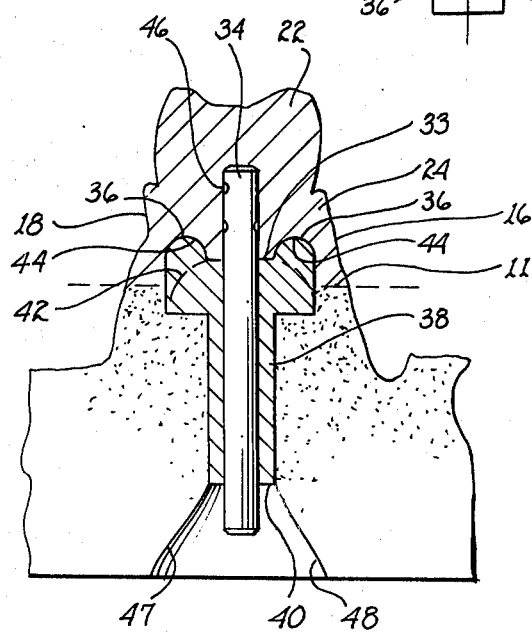
FIG. 3 is a cross-sectional view taken along lines 3—3, as shown in FIG. 2 and including a cross-sectional view of the adjacent parts of a dental model wherein the insert might be lodged.

As may be noted from FIG. 3, base 40 of insert 30 is exposed by walls 47 and 48 in base 12 rather than being covered by the material of the base. Such exposure permits evacuation and discharge of any debris, dust or other contaminants from passageway 32 which may have dropped into the passageway on insertion of pin 34 into the passageway. If this debris remained in the passageway, it would affect the guiding capability of the pin within the passageway and affect seating of the model tooth.

To form base 12 and die 14, the following process may be employed. A pourable casting stone, known as a "pink stone" amongst the cognoscente, is poured into a negative impression up to at least the base of the tooth and preferrably including a part of the buccal and lingual walls. This pink stone when cured, represents die 14. After the pink stone has been compacted to preclude voids and to remove any air bubbles, insert 30, including pins 34 protruding therefrom, is placed upon the exposed surface of the die and forced thereinto until studs 36 and a portion of upper surface 32, including surface 42, is imbedded in the pink stone along with the portions of pins 34 protruding from upper surface 32. After the pink stone is at least partially cured, wax or similar release agent is swathed upon the exposed surface of the pink stone adjacent the partially imbedded insert. Thereafter, additional pourable hardenable stone, generally referred to as "yellow stone" by the cognoscente, is poured within the impression to cover the pink stone and base 38 of the insert. If surface 40 of base 38 of the insert is covered by the yellow stone, a portion of the base is ground away after curing to develop walls 47 and 48 and expose surface 40 along with the openings to the passageways disposed therein. As described above, the wax or other release agent disposed intermediate the pink stone and yellow stone permits removal of any portion of pink stone intermediate mesial and distal cuts which extend below junction 11.

While the principles of the invention have now been made clear in an illustrative embodiment, there will be immediately obvious to those skilled in the art many modifications of structure, arrangement, proportions, elements, materials, and components, used in the practice of the invention which are particularly adapted for specific environments and operating requirements without departing from those principles.

I claim:

1. A dental model for maintaining a removable model tooth in registration within a die mounted upon a base of a dental model, said dental model comprising in combination:
    (a) a pin attached to and extending from the model tooth for guiding the model tooth into a seated relationship with the die upon the base;
    (b) an elongated insert extending commensurate with a plurality of model teeth and rigidly set in said base, said insert extending into both the base and the die on either side of a line of demarcation therebetween, said insert including:
        i. an upper section extending commensurate with the length of said insert, said upper section being releasably connected to the die and extending above the line of demarcation;
        ii. a lower section extending commensurate with the length of said insert, said lower section depending from said upper section into the base and fixed therein below the line of demarcation to maintain structural continuity of said insert despite saw cuts made therein to a depth below the line of demarcation to isolate a model tooth within the die; and
        iii. a series of cylindrical passageways one of which slidably receives said pin for maintaining the alignment of said pin during engagement and disengagement of the model tooth with the die; and
    (c) a series of studs formed as part of said upper section of said insert, at least one stud positioned next to each of said passageways and extending upwardly into and releasably registering with corresponding cavities formed in the die and the model tooth to ensure dimensional stability by cooperation with said passageway for registering the model tooth upon the base and with the die upon seating of the model tooth.

2. The dental model as set forth in claim 1 wherein said series of passageways are aligned centrally along said insert and extend through both said upper and lower sections and wherein said series of stud means comprises two series of studs flanking said series of passageways.

3. The dental model as set forth in claim 2 wherein said upper and lower sections of said insert define a "T" shape in cross-section.

* * * * *